United States Patent
Ichihara et al.

(10) Patent No.: US 9,180,058 B2
(45) Date of Patent: Nov. 10, 2015

(54) DISPOSABLE WEARING ARTICLE

(75) Inventors: Keiko Ichihara, Kagawa (JP); Toshiya Yago, Kagawa (JP); Naoto Ohashi, Kagwa (JP); Makoto Suekane, Kagawa (JP); Hiroki Ishikawa, Kagawa (JP)

(73) Assignee: Unicharm Corporation, Ehime (JP)

( * ) Notice: Subject to any disclaimer, the term of this patent is extended or adjusted under 35 U.S.C. 154(b) by 256 days.

(21) Appl. No.: 13/812,188

(22) PCT Filed: Jul. 19, 2011

(86) PCT No.: PCT/JP2011/066305
§ 371 (c)(1),
(2), (4) Date: Jan. 25, 2013

(87) PCT Pub. No.: WO2012/017813
PCT Pub. Date: Feb. 9, 2012

(65) Prior Publication Data
US 2013/0123727 A1 May 16, 2013

(30) Foreign Application Priority Data

Aug. 2, 2010 (JP) .................................. 2010-173315

(51) Int. Cl.
*A61F 13/15* (2006.01)
*A61F 13/20* (2006.01)
(Continued)

(52) U.S. Cl.
CPC ............. *A61F 13/42* (2013.01); *A61F 13/514* (2013.01); *A61F 13/51121* (2013.01); *A61F 13/53* (2013.01); *A61F 2013/422* (2013.01)

(58) Field of Classification Search
CPC . A61F 13/42; A61F 13/51121; A61F 13/514; A61F 13/53; A61F 2013/422
USPC ........................................................ 604/361
See application file for complete search history.

(56) References Cited

U.S. PATENT DOCUMENTS 7,102,054 B1 * 9/2006 Cree et al. ...................... 604/378
7,361,802 B2 * 4/2008 Ishikawa et al. ............... 604/361
(Continued)

FOREIGN PATENT DOCUMENTS

EP  0 137 644 A2  8/1984
EP  1 685 816 A1  8/2006
(Continued)

OTHER PUBLICATIONS

European supplementary Search Report from corresponding European application No. 11814443.5 dated Mar. 25, 2014 (5 pgs).
(Continued)

*Primary Examiner* — Jason Flick
*Assistant Examiner* — Aundria Hairell
(74) *Attorney, Agent, or Firm* — Brinks Gilson & Lione

(57) ABSTRACT

A disposable wearing article improved so that leakage of body waste can be prevented, a change in color which might develop in an unused state of the wearing article can be inhibited and actually discharged body exudates can immediately cause an indicator to develop a change of color. A disposable diaper includes a topsheet, a backsheet and a liquid-absorbent structure interposed between these top- and backsheets. The backsheet includes first and second backsheets and the first backsheet is formed on its side facing the liquid-absorbent structure with an indicator adapted to develop a color reaction when the indicator comes in contact with at least one of moisture and body exudates. A plurality of such indicators is arranged to extend in a longitudinal direction and to be spaced apart from each other in a transverse direction. The liquid-absorbent structure includes a liquid-absorbent core and a wrapping sheet adapted to wrap the core. A bottom sheet as a hydrophobic bottom element is interposed between a bottom surface of the core and a bottom region of the wrapping sheet as a hydrophobic bottom element.

7 Claims, 12 Drawing Sheets

(51) Int. Cl.
*A61F 13/42* (2006.01)
*A61F 13/511* (2006.01)
*A61F 13/514* (2006.01)
*A61F 13/53* (2006.01)

(56) References Cited

U.S. PATENT DOCUMENTS

2004/0167489 A1* 8/2004 Kellenberger et al. ... 604/385.01
2007/0100305 A1* 5/2007 Isogai et al. ................ 604/361

FOREIGN PATENT DOCUMENTS

| | | |
|---|---|---|
| JP | 60-52603 | 3/1985 |
| JP | 2007-175390 | 7/2007 |
| JP | 2007-236865 | 9/2007 |
| JP | 2009-232987 | 10/2009 |

OTHER PUBLICATIONS

International Search Report based on PCT application No. PCT/JP2011/066305 dated Sep. 20, 2011 (3 pgs).

* cited by examiner

FIG.7
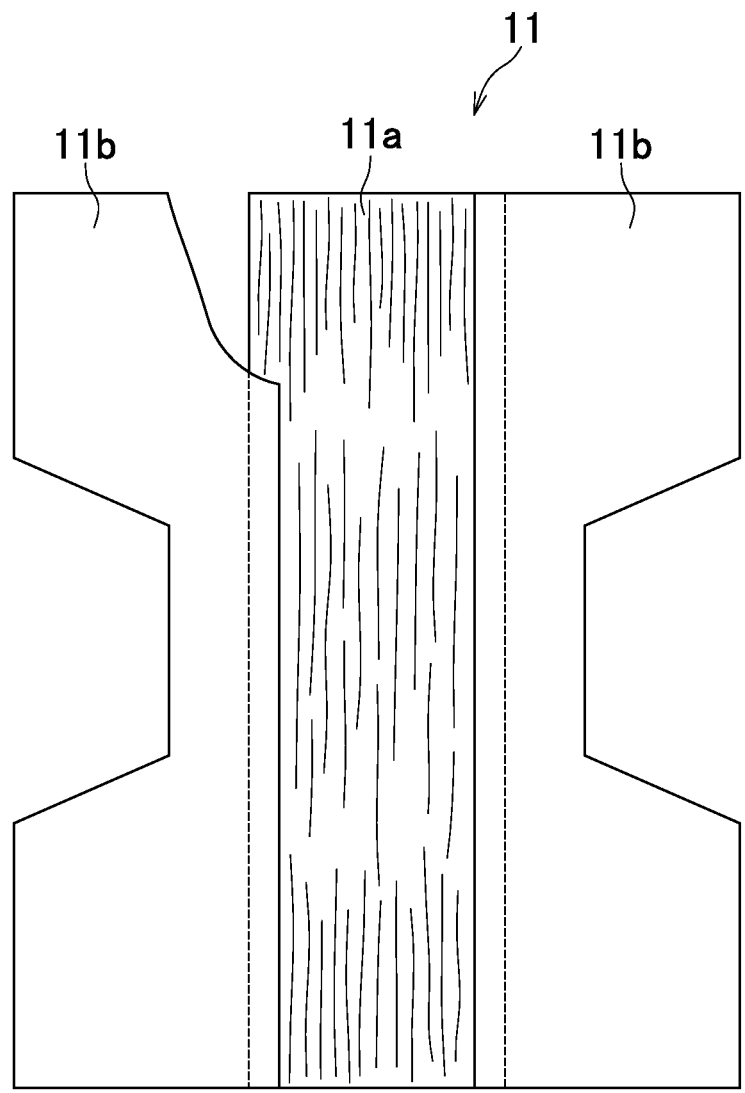
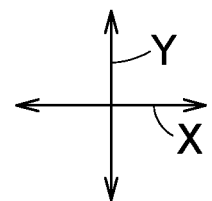

FIG.9
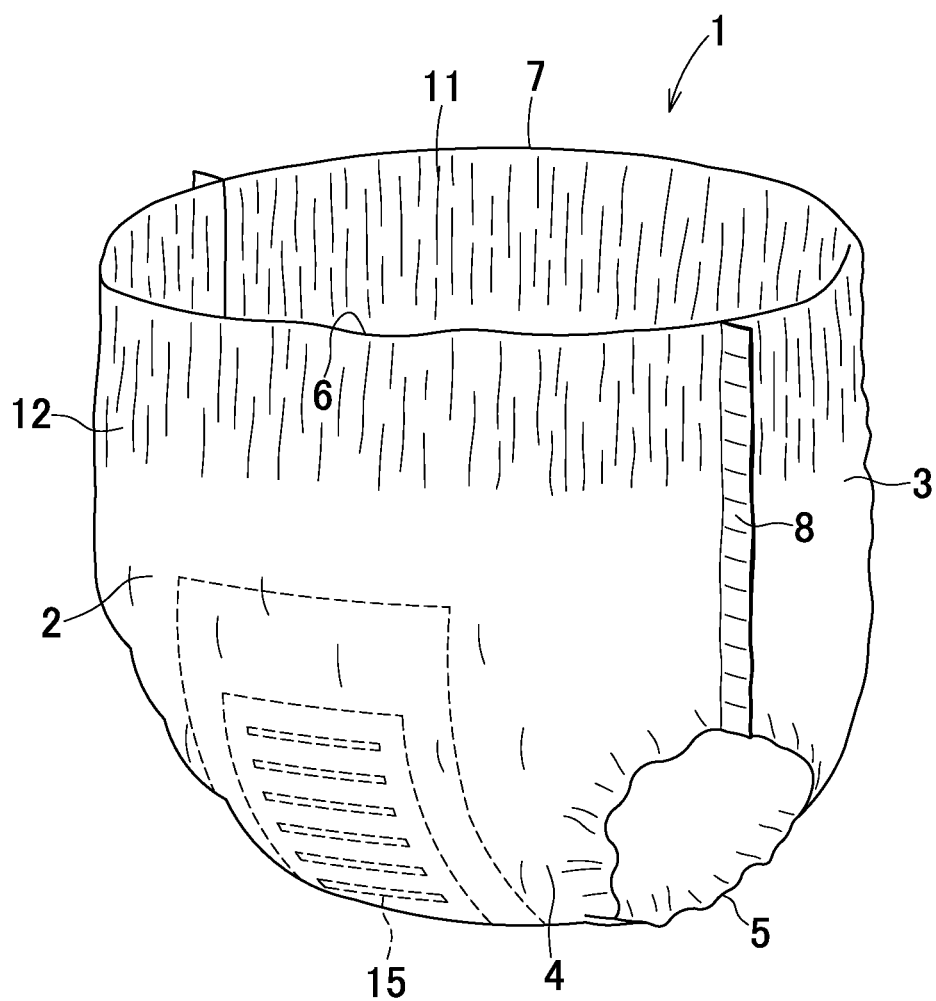
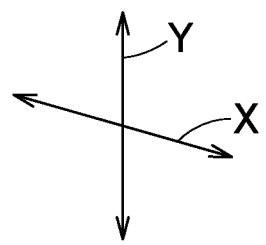

FIG.10
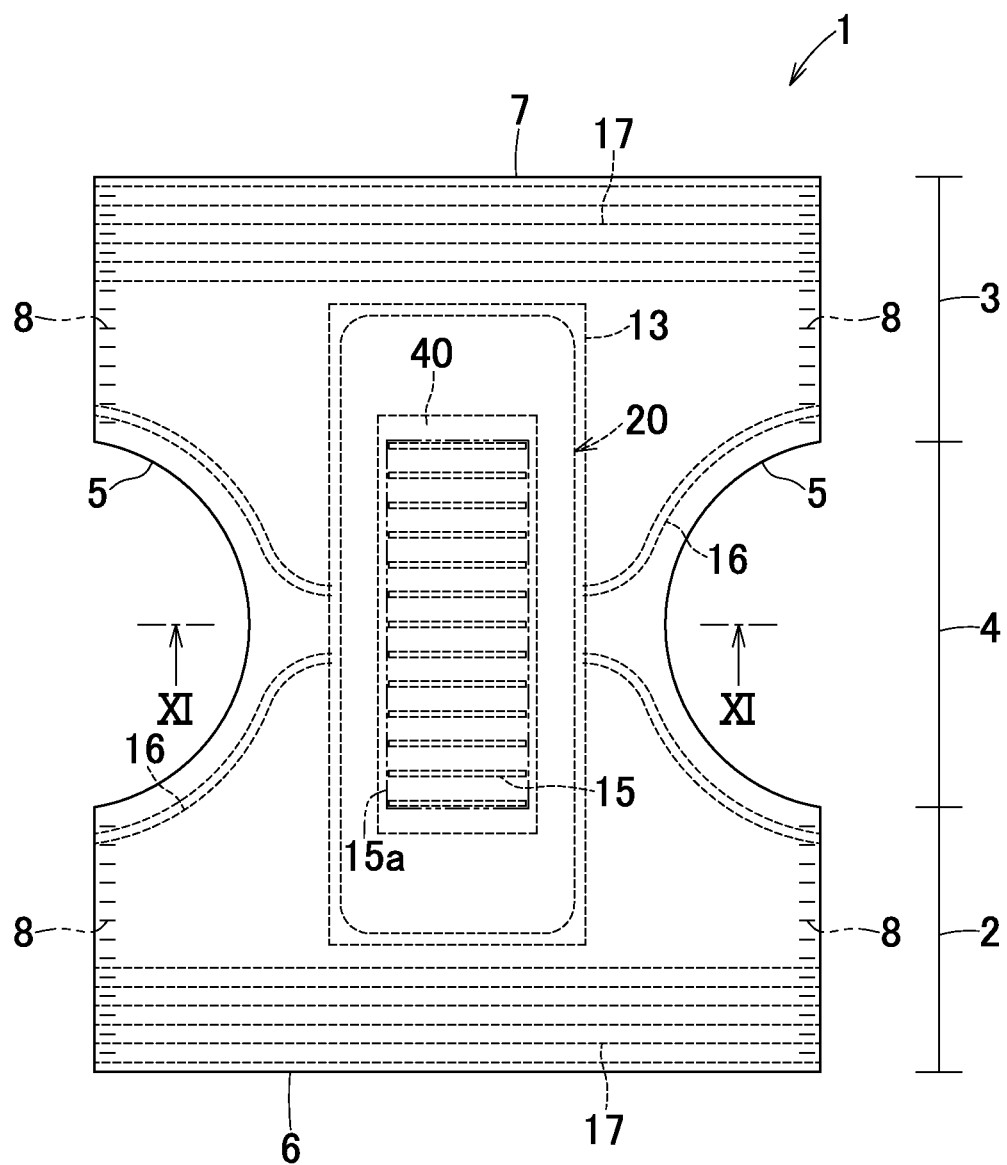
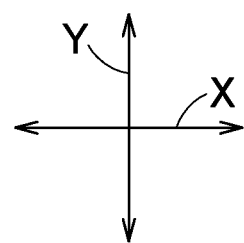

DISPOSABLE WEARING ARTICLE

RELATED APPLICATION

This application is a 35 U.S.C. §371 national phase filing of International Patent Application No. PCT/JP2011/066305, filed Jul. 19, 2011, through which and to which priority is claimed under 35 U.S.C. §119 to Japanese Patent Application No. 2010-173315, filed Aug. 2, 2010.

TECHNICAL FIELD

The present invention relates to disposable wearing articles and more particularly to disposable wearing articles such as disposable diapers, disposable toilet-training pants, disposable incontinent pants or disposable sanitary pants each provided in a crotch region thereof with indicators adapted to develop a color reaction in response to contact with moisture or body exudates.

BACKGROUND

Conventionally, disposable diapers are known including front and rear waist regions and a crotch region extending between these front and rear waist regions wherein the crotch region is formed with an indicator adapted to detect the occurrence of urination. For example, JP 2007-175390 A (PTL 1) discloses a disposable diaper including a crotch region coated with an adhesive containing an ingredient adapted to develop color reaction in response to contact with moisture such as urine so that such an adhesive may function as an indicator.

The disposable diaper described in PTL 1 includes a liquid-absorbent body, a liquid-permeable topsheet lying on the skin-facing side of the absorbent body facing the wearer's body, i.e., the liquid absorbing surface of the absorbent body, a leakage-barrier sheet lying on the bottom side of the absorbent body and a backsheet lying on the outer surface of the leakage-barrier sheet. The absorbent body is wrapped with a wrapping sheet and the side of the leakage-barrier sheet facing the absorbent body is formed with the indicator. As a material of the core wrapping sheet, a hydrophobic fibrous nonwoven fabric is used to prevent the indicator from coming in direct contact with the absorbent body. The absorbent body intrinsically has water absorbability and may absorb moisture vapor in the atmosphere even in an unused state of the diaper. However, the absorbent body may be wrapped with the hydrophobic wrapping sheet to prevent the indicator from undergoing a color change due to moisture vapor in its unused state.

CITATION LIST

Patent Literature

{PTL 1}: JP 2007-175390 A

SUMMARY

Technical Problem

In the disposable diaper disclosed in PTL 1, both the absorbing surface and the bottom surface of the absorbent body are wrapped with the hydrophobic wrapping sheet and, in consequence, body exudates such as urine cannot be smoothly absorbed through the absorbing surface by the absorbent body. As a result, urine staying on the absorbing surface might leak out from the diaper. On the bottom surface, urine having been absorbed by the absorbent body passes through the core wrapping sheet to the indicator and causes the development of color. However, a relatively long time period will be required before the urine reaches the indicator. Thus, there might be a time lag between the occurrence of urination and the arrival of urine at the indicator.

An object of the present invention is to provide a disposable wearing article improved so that the leakage of body waste can be prevented, a change in color which might develop in an unused state of the wearing article can be inhibited and actually discharged body exudates can immediately cause the indicator to develop a change of color.

Solution to Problem

The present invention relates to a disposable wearing article having a longitudinal direction and a transverse direction and including a skin-facing side, a non-skin-facing side opposite to the skin-facing side, front and rear waist regions, a crotch region extending between the front and rear waist regions, a liquid-permeable topsheet lying on the skin-facing side, a liquid-impermeable backsheet lying on the non-skin-facing side and a liquid-absorbent structure interposed between these top- and backsheets and placed at least in the crotch region, wherein the backsheet is provided on the surface thereof facing the liquid-absorbent structure with at least one indicator adapted to develop a color reaction when the at least one indicator comes in contact with at least one of moisture and body exudates.

The present invention further includes the following features:

the topsheet is formed of a fibrous nonwoven fabric in which most of fibers of the fibrous nonwoven fabric has a fiber orientation along one of the longitudinal direction and the transverse direction and an area in which the at least one indicator is provided extends in one of the longitudinal direction and the transverse direction so that the direction of the at least one indicator's area substantially coincides with the fiber orientation of the topsheet;

the liquid-absorbent structure includes a liquid-absorbent core and a wrapping sheet adapted to wrap the skin-facing side and the non-skin-facing side of the core and being continuous outboard of the core in the transverse direction; and between the non-skin-facing side of the core and the wrapping sheet, a hydrophobic bottom element is located to overlap with the at least one indicator and the indicator contains a hot melt polymer and an indicating agent and is provided at least in the crotch region.

According to one embodiment of the present invention, the bottom element is a bottom sheet formed of a sheet material.

According to another embodiment of the present invention, a dimension in the transverse direction of the bottom element is larger than that of the area in which the at least one indicator is provided and smaller than that of the core.

According to even another embodiment of the present invention, a dimension in the longitudinal direction of the bottom element is larger than that of the area in which the at least one indicator is provided.

According to still another embodiment of the present invention, the core contains at least superabsorbent polymer particles and a content percentage of the superabsorbent polymer particles is in a range of 35 to 70% by mass of a total mass of the core.

According to yet another embodiment of the present invention, the bottom sheet has a water bearing pressure in a range of 10 to 350 mmH$_2$O.

According to further another embodiment of the present invention, on lateral portions outboard of the area in the transverse direction in which the at least one indicator is provided, attachment zones extending in the longitudinal direction are provided to provide with the wrapping sheet and the backsheet to each other.

Advantageous Effects of Invention

Particularly according to one or more embodiments of the present invention, the liquid-absorbent structure is interposed between the top- and backsheets and the hydrophobic bottom element is interposed between the non-skin-facing side of the core of the liquid-absorbent structure and the wrapping sheet adapted to wrap this. The backsheet is provided on its side facing the wrapping sheet with at least one indicator which faces the core by the intermediary of the bottom element. With such an arrangement, the bottom element serves to prevent moisture vapor having been absorbed by the core prior to the actual use of the wearing article from causing the at least one indicator to develop a change in color. Upon elimination of body exudates, particularly upon urination, urine quickly passes through the topsheet and the wrapping sheet and is absorbed by the core through the absorbing surface thereof and thus it is possible to prevent urine from leaking out of the wearing article. In addition, urine smoothly moves from the non-skin-facing side of the core along the wrapping sheet to the at least one indicator and therefore it is possible to cause the at least one indicator to develop a change in color substantially without a time lag after urination.

BRIEF DESCRIPTION OF DRAWINGS

FIG. 7 is a plan view illustrating yet another example of the first embodiment.
FIG. 9 is a perspective view illustrating a diaper according to a second embodiment of the disposable wearing article.
FIG. 10 is a view similar to FIG. 2, illustrating the second embodiment.

DESCRIPTION OF EMBODIMENTS

First Embodiment

Figure 1:
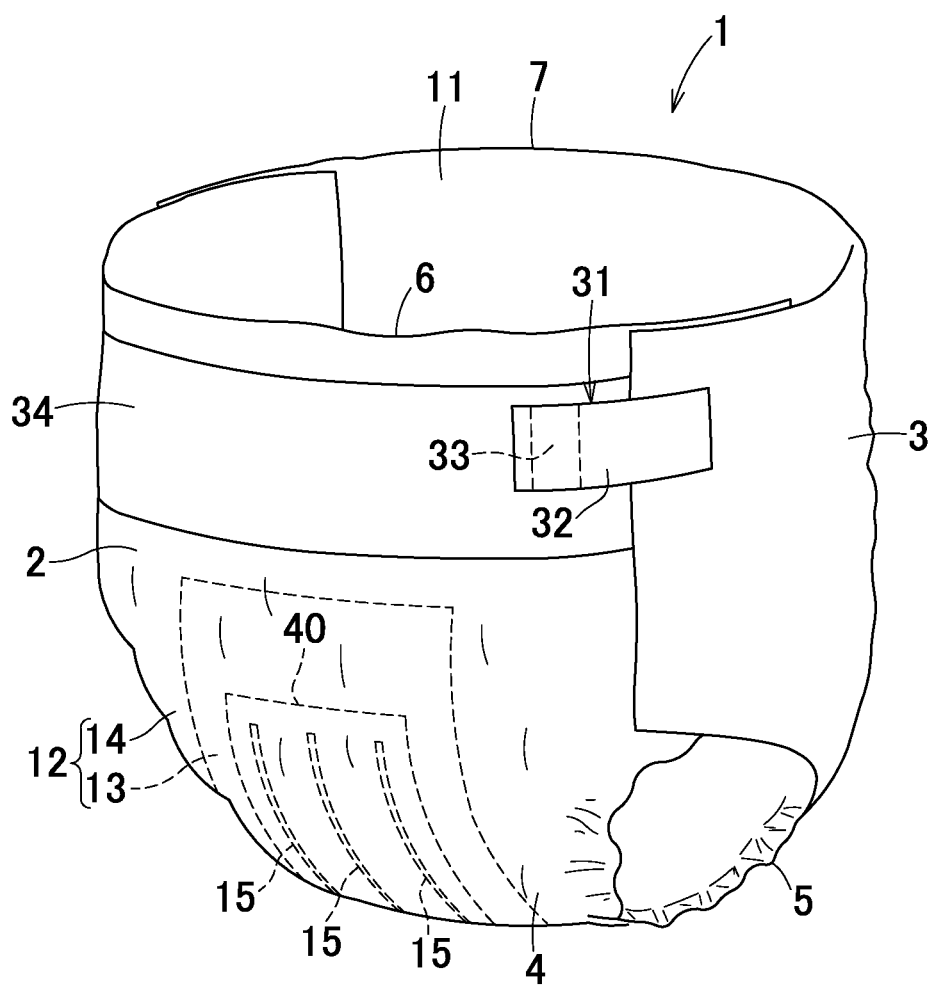
FIG. 1 is a perspective view illustrating a disposable diaper according to a first embodiment of a disposable wearing article.
Figure 2:
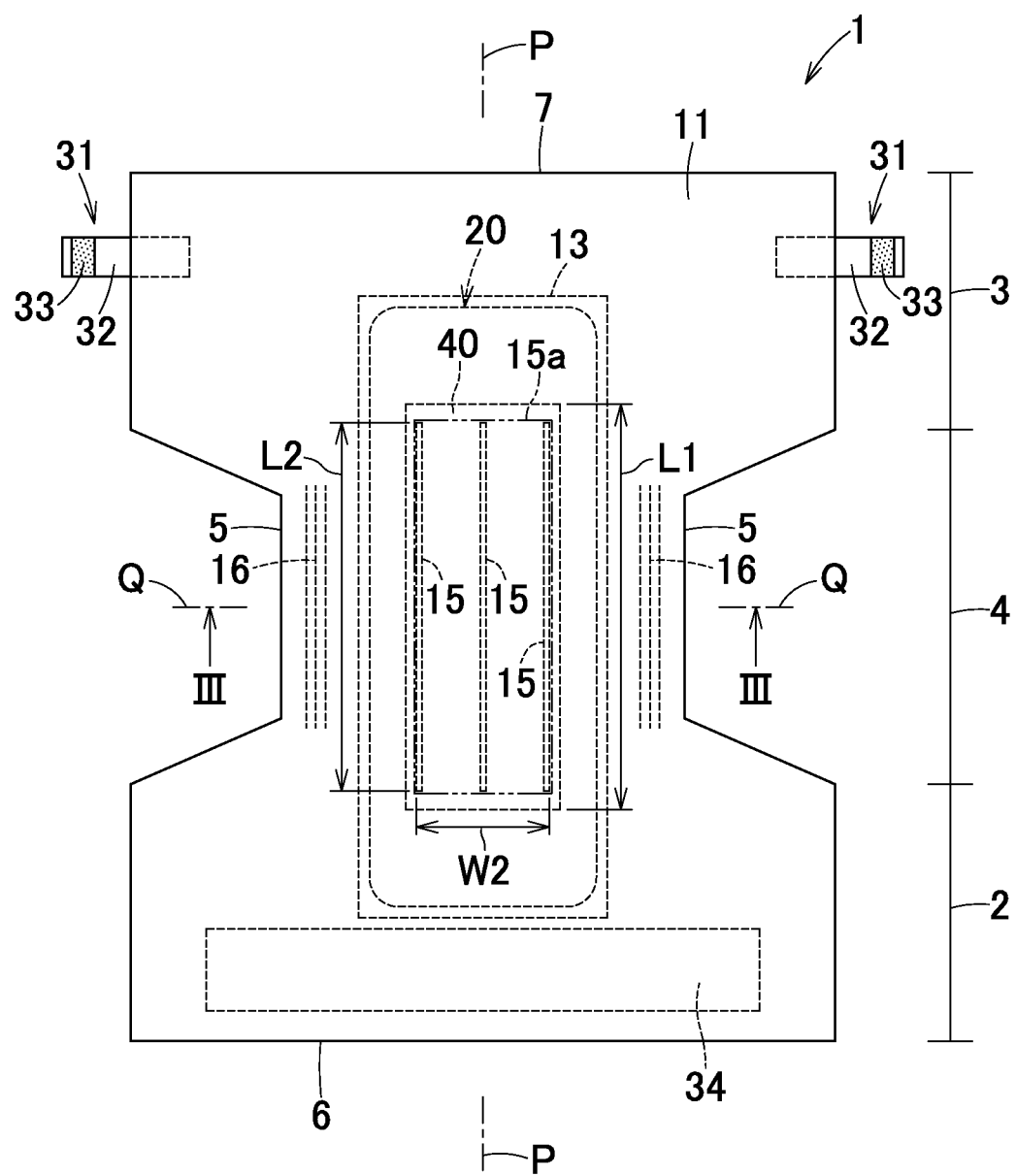
FIG. 2 is a developed plan view of the diaper.
Figure 3:
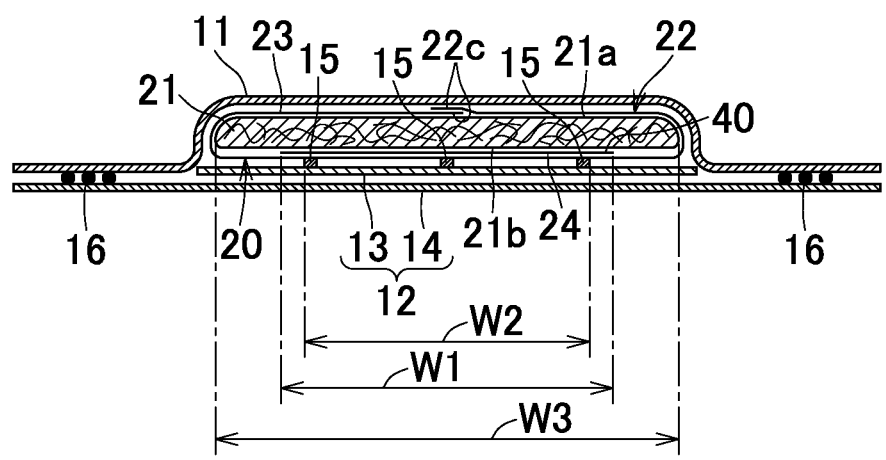
FIG. 3 is a sectional view taken along line III-III in FIG. 2.
Figure 4:
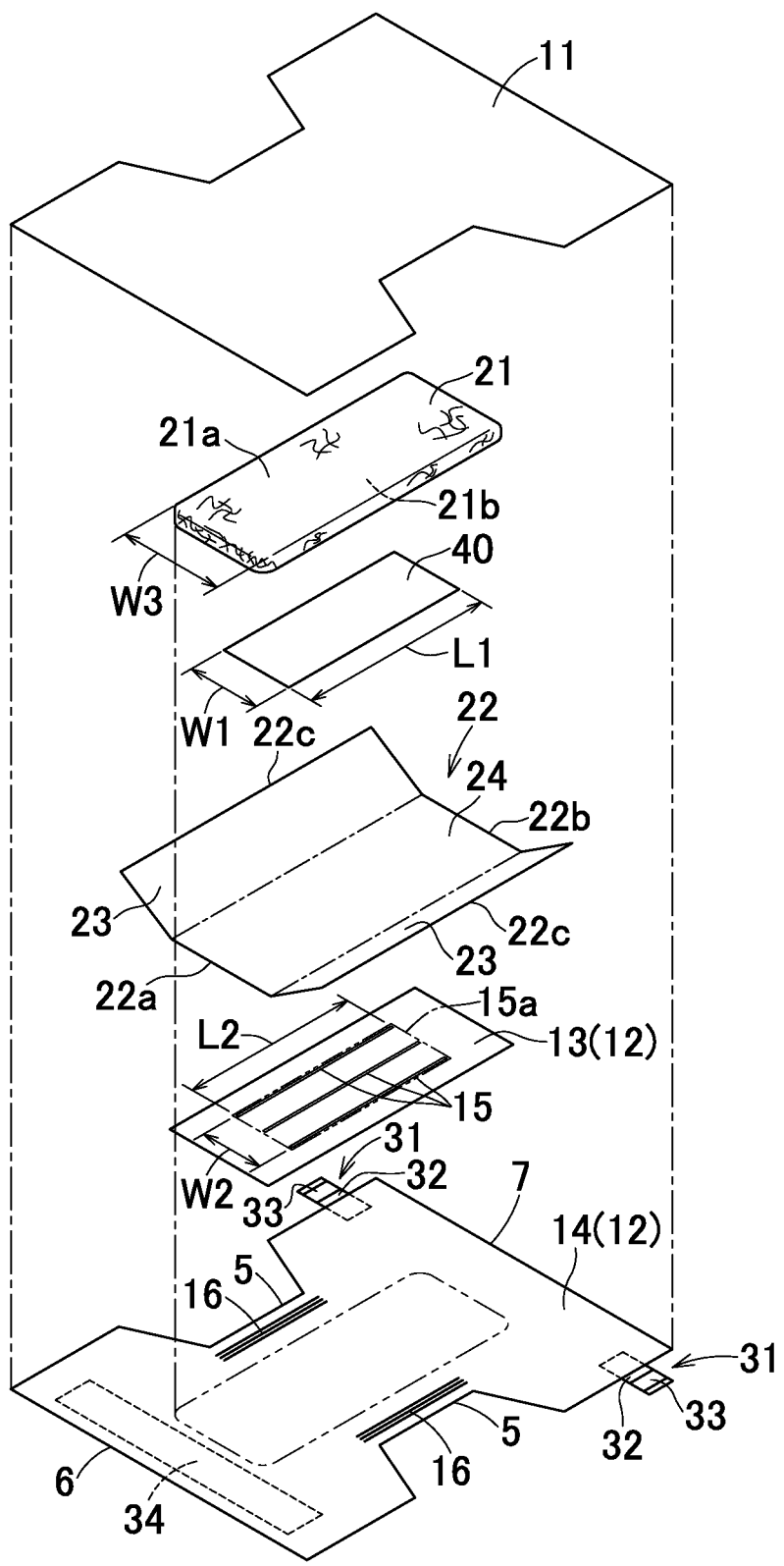
FIG. 4 is an exploded perspective view of the diaper.

FIG. 1 is a perspective view of a disposable diaper 1 illustrated as an example of a disposable wearing article according to the present invention, FIG. 2 is a developed plan view of the diaper 1 as viewed from the side of a wearer's body, FIG. 3 is a sectional view taken along line III-III in FIG. 2 and FIG. 4 is an exploded perspective view of the diaper 1. In FIGS. 2 through 4, respective elastics are illustrated in a state stretched against a contractile force thereof. The diaper 1 has a longitudinal imaginary center line P-P bisecting a dimension of the diaper 1 in a transverse direction X and a transverse imaginary center line Q-Q bisecting a dimension of the diaper 1 in a longitudinal direction Y wherein the diaper 1 is substantially symmetric about the longitudinal imaginary center line P-P.

The diaper 1 has a skin-facing side facing the wearer's body and a non-skin-facing side opposite to the skin-facing side (garment-facing side), a front waist region 2, a rear waist region 3 and a crotch region 4 extending between the front and rear waist regions 2, 3, lateral edges 5 and front and rear ends 6, 7 extending in the transverse direction X in the front and rear waist regions 2, 3, respectively. The diaper 1 includes a liquid-permeable topsheet 11 lying on the skin-facing side, a backsheet 12 lying on the non-skin-facing side and a liquid-absorbent structure 20 interposed between these top- and backsheets 11, 12.

As a material of the topsheet 11, a liquid-permeable fibrous nonwoven fabric may be used and, more specifically, an air-through fibrous nonwoven fabric having a mass per unit area in a range of about 15 to about 35 $g/m^2$ may be used. According to this embodiment, an air-through fibrous nonwoven fabric having a mass per unit area of about 25 $g/m^2$ is used. Most of fibers of such topsheet 11 has previously been uni-directionally oriented by treatments such as carding treatment in a manufacturing process. According to this embodiment, the topsheet 11 is placed so that most of the component fibers of the topsheet 11 may be oriented in the longitudinal direction Y.

As a material of the backsheet 12, a laminate sheet composed of first and second backsheets 13, 14 so that the outer surface of the first backsheet 13 may be covered with the second backsheet 14. The second backsheet 14 is coextensive with the topsheet 11 and it is possible to dimension the first backsheet to be smaller than the second backsheet 14. As a material of the first backsheet 13, for example, a breathable and liquid-impermeable plastic film having a mass per unit area in a range of about 10 to about 25 $g/m^2$. According to this embodiment, the mass per unit area is about 18 $g/m^2$. As a material of the second backsheet 14, a spunbonded/melt-blown/spunbonded (SMS) fibrous nonwoven fabric having a mass per unit area in a range of about 15 to about 35 $g/m^2$ may be used. According to this embodiment, this mass per unit area is about 17 $g/m^2$. By covering the first backsheet 13 with the second backsheet 14, texture of the backsheet 12 can be improved.

The surface of the first backsheet 13 facing the liquid-absorbent structure 20 is provided with a plurality of indicators 15 adapted to develop a color reaction when it comes in contact with at least one of moisture and body exudates. The plurality of indicators 15 extend in the longitudinal direction Y at intervals in the transverse direction and provided on the surface of the first backsheet 13 facing the liquid-absorbent structure 20. In this regard, these indicators 15 may be provided at least in the crotch region 4 and preferably across the crotch region 4 into the front and rear waist regions 2, 3. An area 15a formed with these indicators 15 in this manner extends in the longitudinal direction Y. The area 15a is measured off by a dimension W2 between opposite outermost indicators 15 and a dimension L2 in the longitudinal direction Y of the respective indicators 15. As used herein, the expression "such area 15a extends in the longitudinal direction Y" means that the dimension L2 in the longitudinal direction Y is set to be larger than the dimension W2 in the transverse direction X.

Each of the indicators 15 includes a hot melt adhesive composed of known resins containing a substance adapted to develop a color reaction when it comes in contact with moisture. In other words, the indicators 15 is the hot melt adhesive containing therein an indicator agent adapted to develop a color reaction. As a base polymer of such hot melt adhesive, the polymer widely used for commonly used hot melt adhesives such as polyethylene glycol may be used. As the indicator agent, a pH-indicating agent such as bromocresol green, ethyl red, bromophenol blue or resazurin may be used. It is possible to use the indicators 15 containing therein a thickener resin, a plasticizing oil or a wax diluting solvent.

A plurality of leg elastics 16 extending in the longitudinal direction Y is cooperatively attached between the top- and backsheets 11, 12. More specifically, these leg elastics 16 are contractibly secured under tension in the longitudinal direction Y along the lateral edges 5 of the diaper 1 between the top- and backsheets 11, 12 to extend across at least the crotch region 4. The leg elastics 16 are secured to at least one of the top- and backsheets 11, 12 by an attachment means such as a hot melt adhesive (not shown). Under the effect of these leg elastics 16 secured in such a manner, it is possible to put the lateral edges of the diaper 1 in close contact with vicinities of the wearer's thighs, thereby preventing body waste such as urine and/or feces from leaking out from these regions.

The non-skin-facing side of the backsheet 12 is provided with a pair of first fastening means 31. The first fastening means 31 are attached to the rear waist region 3 and each of the first fastening means 31 includes a tape tab 32 extending outward in the transverse direction X from the backsheet 12 and hook elements 33 attached to a distal portion. The non-skin-facing side of the backsheet 12 in the front waist region 2 is provided with a second fastening means 34 adapted to be releasably engaged with the first fastening means 31. The second fastening means 34 includes loop elements adapted to be releasably engaged with the hook elements 33 and extends in the transverse direction X between the lateral edges 5. The first fastening means 31 may put in engagement with the second fastening means 34 to configure the pants-type diaper 1.

As illustrated in FIGS. 3 and 4, the liquid-absorbent structure 20 includes a liquid-absorbent core 21 and a wrapping sheet 22 used to wrap the core 21. The core 21 has an absorbing surface 21a lying on the skin-facing side, i.e., the side of the topsheet 11 and a bottom surface 21b lying on the non-skin-facing side opposite to the absorbing surface 21a, i.e., on the side of the backsheet 12. As a material of the core 21, for example, fluff wood pulp and superabsorbent polymer particles may be used and, according to this embodiment, a mixture of fluff wood pulp and superabsorbent polymer particles is used. The content of superabsorbent polymer particles may be in a range of about 35 to about 70% by mass of a total mass of the core 21 and preferably in a range of about 45 to about 55% by mass.

The wrapping sheet 22 has front and rear ends 22a, 22b extending in the transverse direction X and lateral edges 22c extending in the longitudinal direction Y wherein the lateral edges 22c are folded onto each other on the absorbing surface 21a. The wrapping sheet 22 includes absorbing regions 23 adapted to wrap the absorbing surface 21a of the core 21 and a bottom region 24 adapted to wrap the bottom surface 21b, wherein these absorbing regions 23 and the bottom region 24 are formed of a single sheet folded outboard of the core 21 in the transverse direction X so as to be integrally continuous. As a material of the wrapping sheet 22, for example, tissue paper preferably having a mass per unit area in a range of about 10 to about 25 $g/m^2$ and Klemm water absorbency of about 20 mm or higher according to JIS-P8141 is preferably about 20 mm or higher.

Between the bottom surface 21b of the core 21 and the bottom region 24 of the wrapping sheet 22, a bottom sheet 40 is interposed so as to function as a hydrophobic bottom element. As a material of the bottom sheet 40, for example, a plastic film or a hydrophobic fibrous nonwoven fabric not treated to become hydrophilic may be used. Specifically, as a material of the plastic film, some types of plastic films such as a plastic film made of polyethylene, polypropylene or polyethylene terephthalate (PET) may be used and such a film may be treated to become microporous to ensure a high breathability. As a material of the fibrous nonwoven fabric, for example, a spunbonded fibrous nonwoven fabric or a spunbonded/meltblown/spunbonded (SMS) fibrous nonwoven fabric each having amass per unit area in a range of about 10 to about 25 $g/m^2$ may be used.

A dimension W1 in the transverse direction X of the bottom sheet 40 is larger than the dimension W2 in the transverse direction X of the area 15a provided with the indicators 15 and smaller than a dimension W3 in the transverse direction X of the core 21. A dimension L1 in the longitudinal direction Y of the bottom sheet 40 is larger than the dimension L2 in the longitudinal direction Y of the indicator 15. The water bearing pressure of the bottom sheet 40 is in a range of about 10 to about 350 $mmH_2O$ and preferably in a range of about 50 to about 250 $mmH_2O$.

The water bearing pressure was measured in accordance with JIS-L1092. Specifically, a piece of the bottom sheet cut off in 160 mm×160 mm was used as a test piece and a level gauge filled with distilled water is moved upward at a rate of 10 cm/min. A water level indicated by a meter at a moment a drop of water appears on the surface of the test piece was measured as a value of the water bearing pressure.

In the diaper 1 as has been described above, the core 21 contains the superabsorbent polymer particles having a particularly high water absorbability and whereby these particles might absorb water vapor in the atmosphere. However, the hydrophobic bottom sheet 40 having a water bearing pressure as high as about 10 mm $H_2O$ or higher is present between the core 21 and the indicator 15 and this bottom sheet 40 can prevent the water vapor within the core 21 from permeating the bottom sheet 40, thereby preventing the indicator 15 from developing the color reaction due to such water vapor.

During use of the diaper 1, upon excretion of body exudates such as urine, urine moves from the liquid-permeable topsheet 11 to the absorbing zone 23 of the wrapping sheet 22 and then is absorbed by the core 21 through the absorbing surface 21a thereof. The water bearing pressure of the bottom sheet 40 is lower than about 350 mm $H_2O$ and therefore urine absorbed by the core 21 can permeate the bottom sheet 40 under the wearer's body weight. Urine permeated the bottom sheet 40 moves to the side of the backsheet 12, comes in contact with the indicators 15 and causes the indicators 15 to develop a change of color. The bottom sheet 40 is hydrophobic and it is more difficult for urine to permeate this bottom sheet 40 than the other sheets or regions. However, the wrapping sheet 22 having a high diffusing capacity enables urine to be diffused over the bottom region 24. Because the bottom region 24 is interposed between the bottom sheet 40 and the indicators 15, the diffused urine comes in contact with the indicators 15 through the bottom region 24 and thereupon causes the indicators 15 to develop a change in color. In this way, the undesirable time lag between the occurrence of urination and the change in color developed by the indicator can be prevented.

The topsheet 11 is placed so that most of the component fibers thereof may be oriented in the longitudinal direction Y and the area 15a in which the indicators 15 are provided may be also oriented in the longitudinal direction Y. In other words, the direction in which most of the component fibers of the topsheet 11 are oriented is the same as the direction in which the area 15a provided with the indicators 15 extends. An amount of urine discharged onto the topsheet 11 is diffused in the longitudinal direction Y along the orientation of most of the component fibers of the topsheet 11. Urine diffused in this manner reaches the indicators 15 by the intermediary of the liquid-absorbent structure 20 and comes in contact with the indicators 15 and causes the indicators 15 to develop a change in color over the relatively large area 15a since this area 15a provided with the indicators 15 extend also in the longitudinal direction Y. the change in color developed by the indicators 15 over a wide range can further improve a visibility of the indicators 15.

According to this embodiment, when an amount of urine discharged is relatively small, urine cannot permeate the bottom sheet 40 and comes in contact with the indicators 15 only by the intermediary of the bottom region 24 of the wrapping sheet 22. In the bottom region 24, such poor amount of urine will move in the transverse direction X from the outer side toward the inner side and, in consequence, only the indicators 15 on lateral portions develop a change of color but the central indicator 15 develops no change of color as the case may be. In such case, it is also possible to determine the amount of urination depending on degrees of a change in color in the respective indicators 15 arranged in the transverse direction X at the regular intervals.

Attachment means such as a hot melt adhesive (not shown) used to attach the bottom region 24 and the backsheet 12 to each other in this embodiment is preferably applied at certain intervals in order to ensure that the urine flow is not impeded by such attachment means.

A percentage by mass of the superabsorbent polymer particles in the core 21 is set to a relatively high rate in a range of about 35 to about 70% by mass. With such a proportion, a thickness dimension of the core 21 can be thereby reduced to about 1.0 to about 3.5 mm. The higher the content percentage of the superabsorbent polymer particles is, the more the behavior of the core 21 to absorb moisture vapor in the atmosphere is correspondingly enhanced. However, with the use of the bottom sheet 40, it is reliably possible to prevent moisture vapor having been absorbed by the core 21 prior to the actual use of the diaper 1 from causing the indicators 15 to develop a change of color. Normally, the superabsorbent polymer particles are mixed with the fluff wood pulp at an appropriate ratio to ensure that the superabsorbent polymer particles are held among the fluff wood pulp fibers and, if the number of the superabsorbent polymer particles exceeds the allowable maximum, the superabsorbent polymer particles could no more be held among the fluff wood pulp fibers and might fall off from the core. Even if the superabsorbent polymer particles having fallen off from the core and are eccentrically-located on the side of the bottom region 24 and these superabsorbent polymer particles absorb the moisture vapor in the atmosphere, it is possible to prevent this moisture vapor from causing the indicators 15 to develop a change in color.

Figure 5:
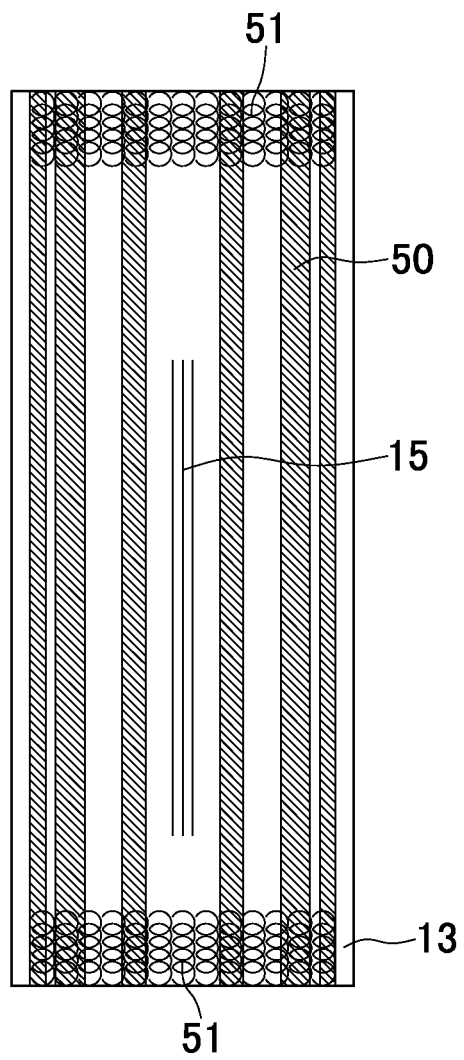
FIG. 5 is a plan view illustrating another example of the first embodiment.
Figure 6:
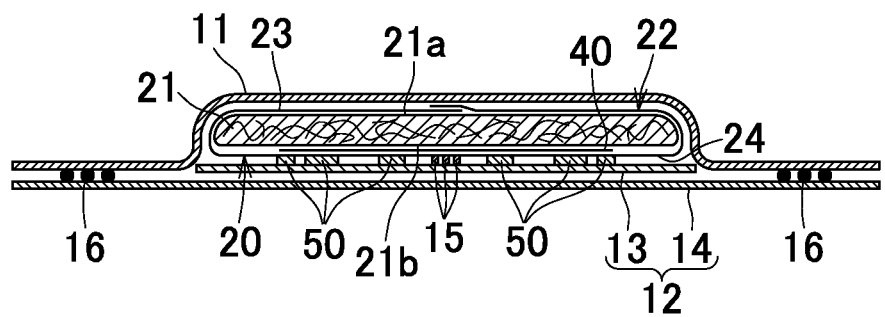
FIG. 6 is a view similar to FIG. 3, illustrating still another example of the first embodiment.

FIGS. 5 and 6 illustrate another example of this embodiment. FIG. 5 is a plan view illustrating the first backsheet 13 as viewed from the side facing the liquid-absorbent structure 20 and FIG. 6 is a sectional view similar to FIG. 3, illustrating the diaper 1 provided with this first backsheet 13. In this embodiment, the first backsheet 13 is provided outboard of the indicators 15 in the transverse direction X with a plurality of first attachment zones 50 arranged to extend in the longitudinal direction Y and to be spaced apart from each other in the transverse direction X. These first attachment zones 50 may include a hot melt adhesive applied in a bead-pattern, a solid-pattern, or other suitable pattern. These first attachment zones 50 are provided between the wrapping sheet 22 and the first backsheet 13.

The hot melt adhesive used to define the first attachment zones 50 is of hydrophobic-type and, as a base polymer of this hot melt adhesive, for example, SBS polymers or SIS polymers may be used. The first attachment zones 50 are spaced outward in the transverse direction X from the adjacent indicator 15. The distance dimension from the adjacent indicator 15 is in a range of about 3.0 to about 20.0 mm, preferably in a range of about 5.0 to about 15.0 mm and more preferably in a range of 6.5 to 10.0 mm. A dimension in the transverse direction X of the respective first attachment zones 50 is in a range of about 1 to about 20 mm, preferably in a range of 3 to 13 mm.

The first backsheet 13 is provided, in addition, along end portions thereof opposite in the longitudinal direction Y with second attachment zones 51, respectively. These second attachment zones 51 may include a hot melt adhesive applied to these end portions. The hot melt adhesive may be applied with use of the generalized methods so as to form various patterns such as a spiral-pattern, an omega-pattern, a solid-pattern or a bead-pattern. The second attachment zones 51 are provided between the wrapping sheet 22 and the first backsheet 13 wherein the second attachment zones 51 partially overlap with the first attachment zones 50.

The first backsheet 13 and the wrapping sheet 22 are attached to each other not only by the intermediary of the above-mentioned first and second attachment zones but also by the intermediary of the indicators 15 containing a hot melt adhesive. During use of the diaper 1 having such first backsheet 13, upon occurrence of urination, urine flows from the topsheet 11 to the absorbing region 23 of the wrapping sheet 22 and then is absorbed by the core 21. The bottom sheet 40 lying beneath the bottom surface 21b of the core 21 allows urine to pass therethrough and to come in contact with the indicators 15. A region around the indicator 15 is partitioned by the first backsheet 13, the first attachment zones 50 and the wrapping sheet 22 and, in addition, the bottom sheet 40 is layered on the wrapping sheet 22. With such an arrangement, it is difficult for urine having flown into the region around the indicators 15 to flow further outward at least in the transverse direction X. In consequence, it is assured to cause the indicators 15 to develop a change in color and, at the same time, to prevent urine from leaking out of the diaper.

While the bottom sheet 40 is used as the hydrophobic bottom element in this embodiment, it is also possible to use a hydrophobic hot melt adhesive as the bottom element. When such a hot melt adhesive is used as the bottom element, the side of the bottom region 24 of the wrapping sheet 22 facing the core 21 is coated with this hot melt adhesive. Specifically, the side of the bottom region 24 of the wrapping sheet 22 facing the core 21 is coated along regions overlapping with the indicators 15 with the hot melt adhesive, for example, in a solid-pattern with a mass per unit area in a range of about 15 to about 150 g/m$^2$. Such a mass per unit area is sufficient to prevent the moisture vapor in the atmosphere having been absorbed by the core 21 from passing through the bottom region 24 coated with such a hot melt adhesive. As the base polymer for this hot melt adhesive, for example, SBS polymers or SIS polymers may be used.

When the hot melt adhesive is used as the bottom element and the indicators 15 arranged to be spaced apart from each other in the transverse direction X, the hot melt adhesive may be applied in association with these respective indicators 15. With such an arrangement, upon occurrence of urination, urine can flow into a space between each pair of the adjacent indicators and thereby can cause further rapidly the respective indicators to develop a change in color. In addition, it is unnecessary to coat the regions defined between the adjacent indicators 15 with the hot melt adhesive and waste of material can be correspondingly cut away. Compared to where a sheet is used, the use of the hot melt adhesive makes it possible to change the position of the bottom element's region more easily and to become more quickly compatible with various types of the indicators 15. The hot melt adhesive is preferably applied over a width about 5 mm or more larger than a dimension in the transverse direction X of the indicators 15 and over a length about 20 mm longer than a dimension in the longitudinal direction Y of the indicator 15, namely, the hot melt adhesive extends outward beyond opposite ends of the indicators 15 by about 10 mm, respectively.

The hot melt adhesive may be applied as the bottom element between the bottom surface 21b of the core 21 and the wrapping sheet 22 to attach these bottom surface 21b and the wrapping sheet 22 to each other. As a result, displacement of the core 21 can be prevented. In addition, this hot melt adhesive makes it possible to bond the fluff wood pulp and the superabsorbent polymer particles composing the core 21 to each other. In consequence, it is also possible to prevent the core 21 from losing its initial configuration.

Figure 8:
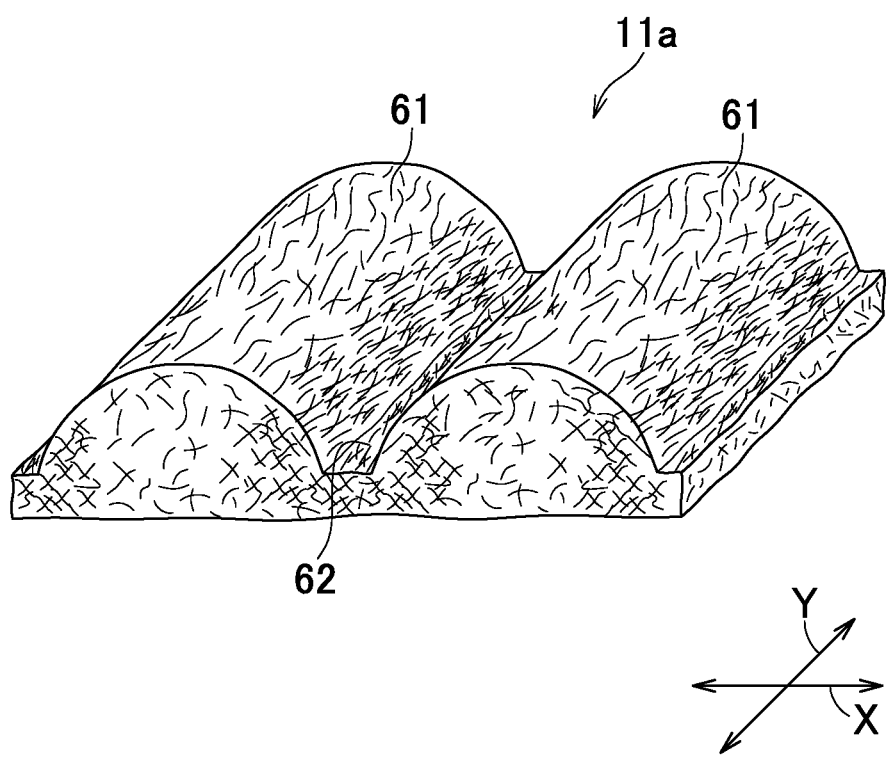
FIG. 8 is a scale-enlarged perspective view illustrating part of FIG. 7.

FIGS. 7 and 8 illustrate still another example of the embodiment wherein FIG. 7 is a partially cutaway plan view of the topsheet 11 and FIG. 8 is an scale-enlarged perspective view illustrating part of a central sheet 11a of the topsheet 11. According to the embodiment, the topsheet 11 includes a generally rectangular central sheet 11a composed of fibers oriented in the longitudinal direction Y and opposite lateral sheets 11b lying outboard of the central sheet 11a in the transverse direction X. At least the central sheet 11a is formed of a liquid-permeable fibrous nonwoven fabric characterized by including a plurality of ridges 61 extending in the longitudinal direction Y and a plurality of grooves 62 defined between each pair of the adjacent ridges 61 and extending in the longitudinal direction Y. The lateral sheets 11b may be formed of a liquid-permeable or liquid-impermeable fibrous nonwoven fabric. The other arrangements are similar to those in the diaper 1 illustrated in FIGS. 1 through 4.

The central sheet 11a may be provided with the ridges 61 and the grooves 62, for example, by subjecting the regions of the central sheet 11a to be provided with the grooves 62 to gaseous fluid jets, for example, hot air jets. By subjecting the sheet 11a to the above-mentioned fluid jets, the fibers in the respective grooves 62 are forcibly drifted toward lateral portions while the fibers in the respective grooves 62 substantially maintaining the orientation thereof in the longitudinal direction Y. In this way, the oriented fibers are more than the fibers oriented in the transverse direction X in the central sheet 11a and, as a whole, the fiber orientation in the longitudinal direction X can be conspicuous.

A dimension in the transverse direction X of the central sheet 11a is preferably equal to or larger than a dimension in the transverse direction X of the core 21. Measurement of the fiber orientation of the central sheet 11a may be carried out, for example, with use of Digital Microscope VHX-100 manufactured by Keyence Corporation. Specifically. within a certain definite range of the observed image data, the fibers falling within the range of +45° to −45° to imaginary lines extending in parallel in the longitudinal direction is determined to be oriented in the longitudinal direction and the fibers falling within the range of +45° to −45° to imaginary lines extending in parallel in the transverse direction are determined to be oriented in the transverse direction. A percentage of total number of fibers oriented in the longitudinal direction and a percentage of total number of fibers oriented in the transverse direction may be calculated to measure/calculate the fiber orientation. For example, if the number of fibers observed to be oriented in the longitudinal direction is 55% or more of the total number of fibers, i.e., 100%, it may be determined that the sheet has the fiber orientation along the longitudinal direction. In this regard, the method for determination of the fiber orientation is not limited to the above-mentioned measurement and it is also possible to determine the fiber orientation by measuring a tensile force of the sheet. Specifically, a test piece extending in the longitudinal direction of the sheet and a test piece extending in the transverse direction may be prepared and tensile strength under a predetermined tensile load may be measured with use of a tensile tester. If the tensile strength of the test piece extending in the longitudinal direction is higher than that of the test piece extending in the transverse direction, it may be determined that the sheet has the fiber orientation along the longitudinal direction.

Second Embodiment

Figure 11:
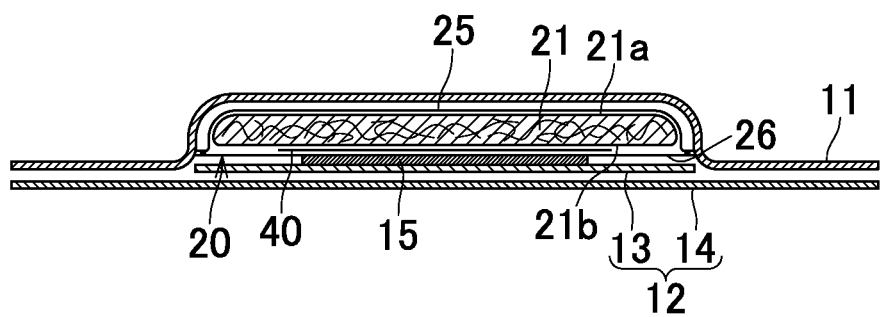
FIG. 11 is a sectional view taken along line XI-XI in FIG. 10.
Figure 12:
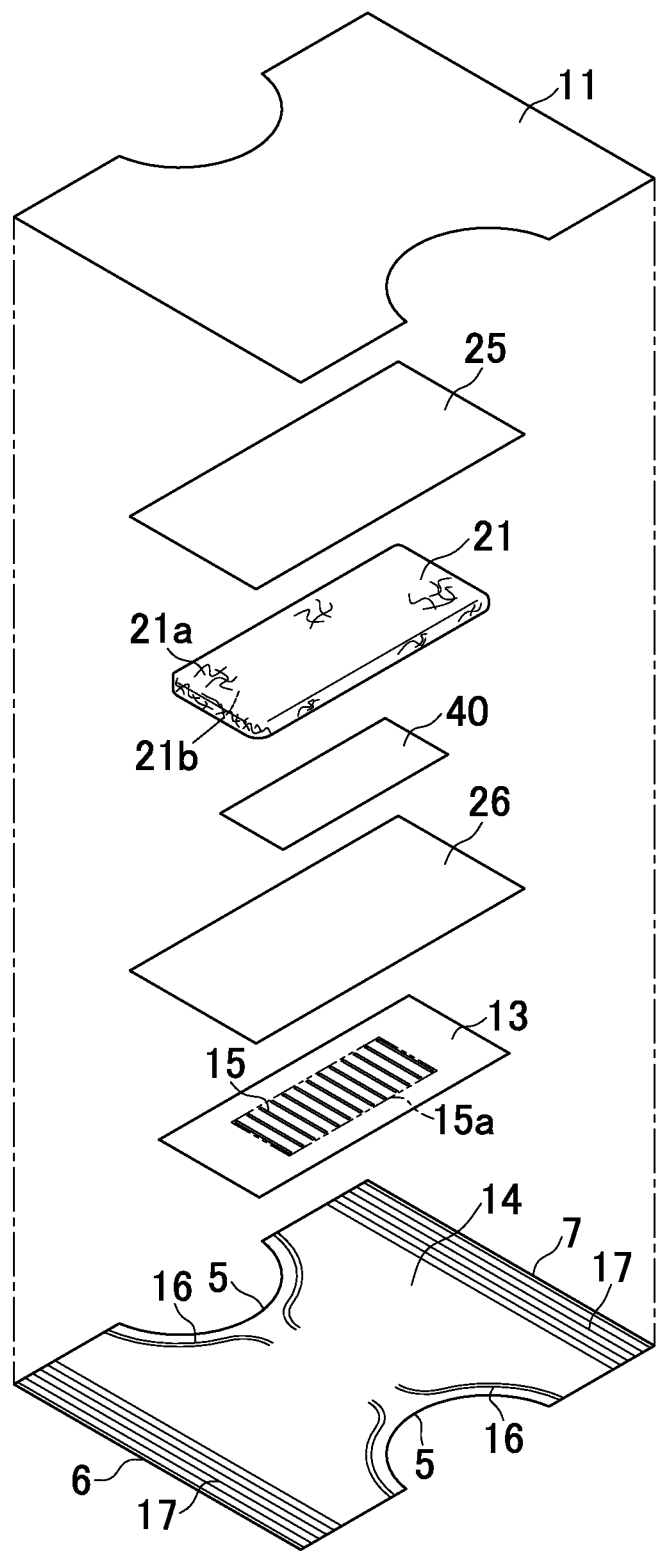
FIG. 12 is a view similar to FIG. 4, illustrating the second embodiment.

FIGS. 9 through 12 illustrate a second embodiment of the present invention. FIG. 9 is a perspective view of the diaper 1 similar to FIG. 1, illustrating the diaper 1 according to this embodiment, FIG. 10 is a developed plan view of the diaper 1 similar to FIG. 2, FIG. 11 is a sectional view taken along line XI-XI in FIG. 10 and FIG. 12 is an exploded perspective view of the diaper 1 similar to FIG. 4. The constituent elements similar to those in the first embodiment are designated by similar reference signs and details thereof will not be repetitively described hereunder.

The diaper 1 is formed along the lateral edges 5 in the front and rear waist regions 2, 3 with a series of seams 8 at which the front and rear waist regions 2, 3 are joined to each other. Thereupon, the front and rear ends 6, 7 cooperate with each other to form a waist-opening and the lateral edges 5 in the crotch region 4 cooperate with each other to form a pair of leg-openings. In this way, a pull-on-type diaper is configured. In the front and rear waist regions 2, 3, a plurality of waist region's elastics 17 extending in the transverse direction X and spaced apart from each other in the longitudinal direction Y are contractibly attached between the top- and backsheets 11, 12 under tension. The crotch region 4 is provided along the lateral edges 5 thereof with leg elastics 16 contractibly attached thereto under tension. Under the effect of contraction of these leg elastics 16 and the waist region's elastics 17, the diaper 1 is kept in close contact with the wearer's body to prevent the leakage of body waste such as urine and/or feces.

The liquid-absorbent structure 20 is interposed between the top- and backsheets 11, 12. The liquid-absorbent structure 20 includes the core 21, a first wrapping sheet 25 adapted to wrap the absorbing surface 21a of the core 21 and a second wrapping sheet 26 adapted to wrap the bottom surface 21b of the core 21. The first and second wrapping sheets 25, 26 are joined to each other along respective side edges and respective front and rear ends by appropriate means or techniques such as hot melt adhesive, heat sealing or ultrasonic sealing techniques wherein these first and second wrapping sheets 25, 26 are contiguous to each other at least outboard of the core 21 in the transverse direction. As a material of these first and second wrapping sheets 25, 26, the same material as the wrapping sheet 22 in the first embodiment may be used. The bottom sheet 40 is interposed between the bottom surface 21b of the core 21 and the second wrapping sheet 26.

The backsheet 12 includes the first backsheet 13 facing the second wrapping sheet 26 and the second backsheet 14 layered on the first backsheet 13 wherein the first backsheet 13 is provided with a plurality of the indicators 15 extending in the transverse direction X and spaced apart from each other in the longitudinal direction Y. The area 15a in which the indicators are provided has a dimension in the transverse direction X smaller than that of the bottom sheet 40 and a dimension in the longitudinal direction Y, i.e., a dimension defined between a pair of the outermost indicators 15 as viewed in the longitudinal direction Y is smaller than a dimension in the longitudinal direction Y of the bottom sheet 40. In other words, the area 15a in which the indicators 15 are provided overlaps with the bottom sheet 40 so as to be fully covered with the bottom sheet 40.

The area 15a in which the indicators 15 are provided has a dimension in the longitudinal direction Y larger than that in the transverse direction X to extend in the longitudinal direction Y. Most of the component fibers of the topsheet 11 have a fiber orientation along the longitudinal direction Y and this fiber orientation coincides with the direction in which the area 15a in which the indicators 15 are provided.

According to this second embodiment, the indicators 15 are arranged to be spaced apart from each other in the longitudinal direction Y and therefore an extent of urine in the longitudinal direction Y can be visually recognized at once on the basis of a change in color developed in the indicators. Specifically, when a voided volume is relatively small, color change is observed only in a group of the indicators 15 facing the wearer's urethral orifice and when a voided volume is relatively large, the number of the indicators 15 developing a change in color correspondingly increases in the longitudinal direction Y. With the indicators 15 arranged so as to be spaced apart from each other in the longitudinal direction Y, such variation can be easily recognized and exchange of the diaper 1 can be well-timed.

An open-type diaper like the first embodiment is often manufactured in a "longitudinal feed mode" in which, for example, the top- and backsheets 11, 12 are conveyed in the longitudinal direction Y and, in contrast, a pull-on-type diaper is often manufactured in a "transverse feed mode" in which, for example, the top- and backsheets 11, 12 are conveyed in the transverse direction X. When the diaper 1 is manufactured in the longitudinal feed mode as in the first embodiment, the first backsheet 13 also is fed in the longitudinal direction Y and the sheet may be coated with the hot melt adhesive used to provide with the indicators 15 along the direction in which the first backsheet 13 is conveyed. In this way, the indicators 15 extending in the longitudinal direction Y can be easily provided. When the diaper 1 is manufactured in the transverse feed mode as in the second embodiment, the first backsheet 13 also is fed in the transverse direction X and the indicators 15 extending in the transverse direction X can be easily provided.

While a plurality of the indicators 15 are provided both in the first embodiment and in the second embodiment, it is not essential to provide with a plurality of the indicators 15 but the number of the indicator 15 may be single. In addition, the indicator (s) 15 is not limited to the linear indicator (s) 15 but it is possible to provide the indicator 15 in the form of graphic or letter. It is also possible to adopt the indicator (s), the wrapping sheet and the bottom element according to the first embodiment in the second embodiment and to adopt the indicator (s), the wrapping sheet and the bottom element according to the second embodiment in the first embodiment.

The constituent elements of the diaper 1 are not limited to those described in this specification but the other types of material widely used in the relevant technical field may be used without limitation. The terms "first" and "second" used in this description are used merely to distinguish the similar elements, similar positions or the other similar means.

REFERENCE SIGNS LIST 1 disposable diaper (disposable wearing article)
2 front waist region
3 rear waist region
4 crotch region
11 topsheet
12 backsheet
15 indicator
20 liquid-absorbent structure
21 core
21a absorbing surface
21b bottom surface
22 wrapping sheet
40 bottom sheet
X transverse direction
Y longitudinal direction

The invention claimed is:

1. A disposable wearing article having a longitudinal direction and a transverse direction, including:
   a skin-facing side;
   a non-skin-facing side opposite to the skin-facing side;
   front and rear waist regions;
   a crotch region extending between the front and rear waist regions;
   a liquid-permeable topsheet lying on the skin-facing side;
   a liquid-impermeable backsheet lying on the non-skin-facing side; and
   a liquid-absorbent structure interposed between these top- and backsheets and placed at least in the crotch region, wherein
   the backsheet is formed on the surface thereof facing the liquid-absorbent structure with at least one indicator adapted to develop a color reaction when the indicator comes in contact with at least one of moisture and body exudates, wherein:
   the topsheet is formed of a fibrous nonwoven fabric of which most of fibers of the fibrous nonwoven fabric has a fiber orientation along one of the longitudinal direction and the transverse direction and an area in which the at least one indicator is provided extends in one of the longitudinal direction and the transverse direction so that the direction of the at least one indicator's area substantially coincides with the fiber orientation of the topsheet;
   the liquid-absorbent structure includes a liquid-absorbent core and a wrapping sheet adapted to wrap the skin-facing side and the non-skin-facing side of the core and being continuous outboard of the core in the transverse direction; and
   between the non-skin-facing side of the core and the wrapping sheet, a hydrophobic bottom element is located to overlap with the at least one indicator and the at least one indicator contains a hot melt polymer and an indicating agent and is provided at least in the crotch region, wherein the hydrophobic bottom element comprises one of:
   a hydrophobic microporous film;
   a hydrophobic nonwoven fabric having a mass per unit area in a range of about 10 to about 25 g/m$^2$; and a hot melt adhesive having a mass per unit area in a range of about 15 to about 150 g/m².

2. The disposable wearing article according to claim 1, wherein the bottom element is a bottom sheet formed of a sheet material comprising one of a hydrophobic microporous film and a hydrophobic nonwoven fabric having a mass per unit area in a range of about 10 to about 25 g/m².

3. The disposable wearing article according to claim 1, wherein a dimension in the transverse direction of the bottom element is larger than that of the area in which the at least one indicator is provided and smaller than that of the core.

4. The disposable wearing article according to claim 1, wherein a dimension in the longitudinal direction of the bottom element is larger than that of the area in which the at least one indicator is provided.

5. The disposable wearing article according to claim 1, wherein the core contains at least superabsorbent polymer particles and a content percentage of the superabsorbent polymer particles is in a range of 35 to 70% by mass of a total mass of the core.

6. The disposable wearing article according to claim 2, wherein the bottom sheet has a water bearing pressure in a range of 10 to 350 mmH₂O.

7. The disposable wearing article according to claim 1, wherein, on both outer sides in the transverse direction of the area in which the indicator is provided, attachment zones extending in the longitudinal direction are formed to attach the wrapping sheet and the backsheet to each other.

\* \* \* \* \*